(12) United States Patent
Stothers et al.

(10) Patent No.: US 8,060,319 B2
(45) Date of Patent: Nov. 15, 2011

(54) ACOUSTIC STRUCTURAL INTEGRITY MONITORING SYSTEM AND METHOD

(75) Inventors: Ian McGregor Stothers, Saham Tomey (GB); Andrew Dargle, Baldock (GB)

(73) Assignee: Ultra Electronics Limited, Greenford, Middlesex (GB)

( * ) Notice: Subject to any disclaimer, the term of this patent is extended or adjusted under 35 U.S.C. 154(b) by 934 days.

(21) Appl. No.: 11/653,095

(22) Filed: Jan. 12, 2007

(65) Prior Publication Data
US 2009/0070048 A1    Mar. 12, 2009

Related U.S. Application Data

(63) Continuation of application No. PCT/GB2005/002784, filed on Jul. 15, 2005.

(30) Foreign Application Priority Data

Jul. 15, 2004   (GB) .................................. 0415855.6

(51) Int. Cl.
*G01N 29/14*    (2006.01)
(52) U.S. Cl. ........................................................ 702/39
(58) Field of Classification Search ...................... 702/39
See application file for complete search history.

(56) References Cited

U.S. PATENT DOCUMENTS

| | | | |
|---|---|---|---|
| 4,043,176 A | 8/1977 | Graham | |
| 4,979,124 A | 12/1990 | Sachse et al. | |
| 5,115,681 A | 5/1992 | Bouheraoua et al. | |
| 5,528,557 A | 6/1996 | Horn | |
| 5,814,729 A * | 9/1998 | Wu et al. .......................... | 73/588 |
| 6,006,163 A | 12/1999 | Lichtenwalner et al. | |
| 6,628,567 B1 | 9/2003 | Prosser et al. | |

OTHER PUBLICATIONS

J. P. Lynch, Overview of Wireless Sensors for Real-Time Health Monitoring of Civil Structures, Source: Proceedings of the 4th International Workshop on Structural Control and Monitoring, New York City, NY, USA, Jun. 10-11, 2004, p. 1-6.*
http://www.merriam-webster.com/dictionary/locate, p. 1, Aug. 27, 2010.*

* cited by examiner

*Primary Examiner* — Tung S Lau
(74) *Attorney, Agent, or Firm* — Dickstein Shapiro LLP

(57) ABSTRACT

A method and system for detecting structural damage in a structure by detecting acoustic emissions from damage in a structure to obtain acoustic emission data, and processing the acoustic emission data in accordance with a model characterising acoustic paths. The model is built by inducing a plurality of types of acoustic emissions at each of a plurality of positions on a structure, the plurality of types of acoustic emissions corresponding to a respective plurality of types of structural damage. The acoustic emissions are detected using at least three sensors arranged on the structure, and the detected acoustic emissions are processed for each position to determine model data characterising effects on each type of acoustic emission from each position of acoustic paths between the positions and the sensors. The processed data is then stored as model data.

17 Claims, 13 Drawing Sheets

ACOUSTIC STRUCTURAL INTEGRITY MONITORING SYSTEM AND METHOD

CROSS-REFERENCE TO RELATED APPLICATION

This application is a continuation of a co-pending international application PCT/GB 2005/002784, with an international filing date of Jul. 15, 2005, entitled, "ACOUSTIC STRUCTURAL INTEGRITY MONITORING SYSTEM AND METHOD", and international application GB/0415855.6, with a filing date of Jul. 15, 2004, entitled, "ACOUSTIC STRUCTURAL INTEGRITY MONITORING SYSTEM AND METHOD" both of which is incorporated by reference herein in its entirety.

TECHNICAL FIELD

The present invention generally relates to a system and method to monitor for structural defects in structures on the basis of acoustic emission from such defects.

BACKGROUND OF THE INVENTION

Stress corrosion and fatigue in structures causes crack growth. This is due to the metal slowly becoming brittle when there is a concentration of stress within a short distance of the crack tip. The crack then advances to a zone boundary in a series of discrete microfracture events, where the microfractures can take place either intergranularly or transgranularly. Tougher undamaged material at the zone boundary stops the crack advancing. The cycle of cracking is then repeated, starting again with a concentration of stress at or near the crack tip.

Under normal operating conditions, damage such as cracking in a structure develops slowly over time. However, if the structure is operating outside its normal range, a large amount of damage may occur within a short time. In addition, damage caused by stress to a structure is not limited to cracking and may also include fretting, pitting and rubbing. It is therefore essential that structures be monitored regularly so that damage may be detected and repaired, or further damage prevented if the damage is not advanced.

Cracking and fracturing is known to cause particular problems in aircraft, pressure vessels and oilrigs, as well as in large structures such as bridges. As cracking occurs, the cracks produce bursts of acoustic energy as wideband ultrasonic emissions in the structure where the cracking is taking place, known as acoustic emissions. The properties of the waveform of the acoustic emissions, such as □t values representing the differences between the times that bursts of acoustic energy are received at different locations, frequency, amplitude, rise time etc are dependent on the size of the crack and how rapidly it propagates through the structure. Therefore cracks can be identified by their acoustic emission signature, which can be detected using acoustic sensors as acoustic emission sensors.

US 2003/0140701, the disclosure of which is hereby incorporated by reference, discloses a method of detecting and monitoring damage in a structure by receiving electrical signals continuously over a period of time as pulses representing a burst of acoustic energy from a plurality of acoustic sensors carried by the structure. The bursts of acoustic energy represent emissions from sites of damage. The burst is processed to obtain a smoothed envelope waveform. Wave-shape information and time information is determined and stored for each burst. If a burst is detected at three or more sensors, the difference in the time of arrival of the bursts at the sensors is determined as □t values. The □t values are then used to accumulate the bursts to determine if a threshold for the bursts is exceeded. If so, the burst data is stored to represent structural damage together with non-acoustic parameters.

However, there is a limitation in this system. When the health of a structure and structural damage is monitored by acoustic emission techniques, errors can occur in the analysis of the data using the system due to the assumption that the speed of sound in structures is uniform in all directions and there is a single mode of acoustic propagation though the structure. However, the speed of sound varies with the thickness and type of material through which the sound is propagating. The speed of propagation of acoustic waves will therefore vary as they propagate through an inhomogeneous structure.

It is therefore an object of one aspect of the present invention to provide a system and method to monitor for structural defects in structures on the basis of acoustic emission from such defects.

SUMMARY OF THE INVENTION

Embodiments of the present invention provide system and method to monitor for structural defects in structures on the basis of acoustic emission from such defects.

One aspect of the present invention provides a method and system for building a model of the effect of acoustic paths in a structure. The model is built by inducing a plurality of types of acoustic emissions at many positions in the structure and by detecting the acoustic emissions using a plurality of acoustic emission sensors that are arranged on the structure.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

Figure 1:
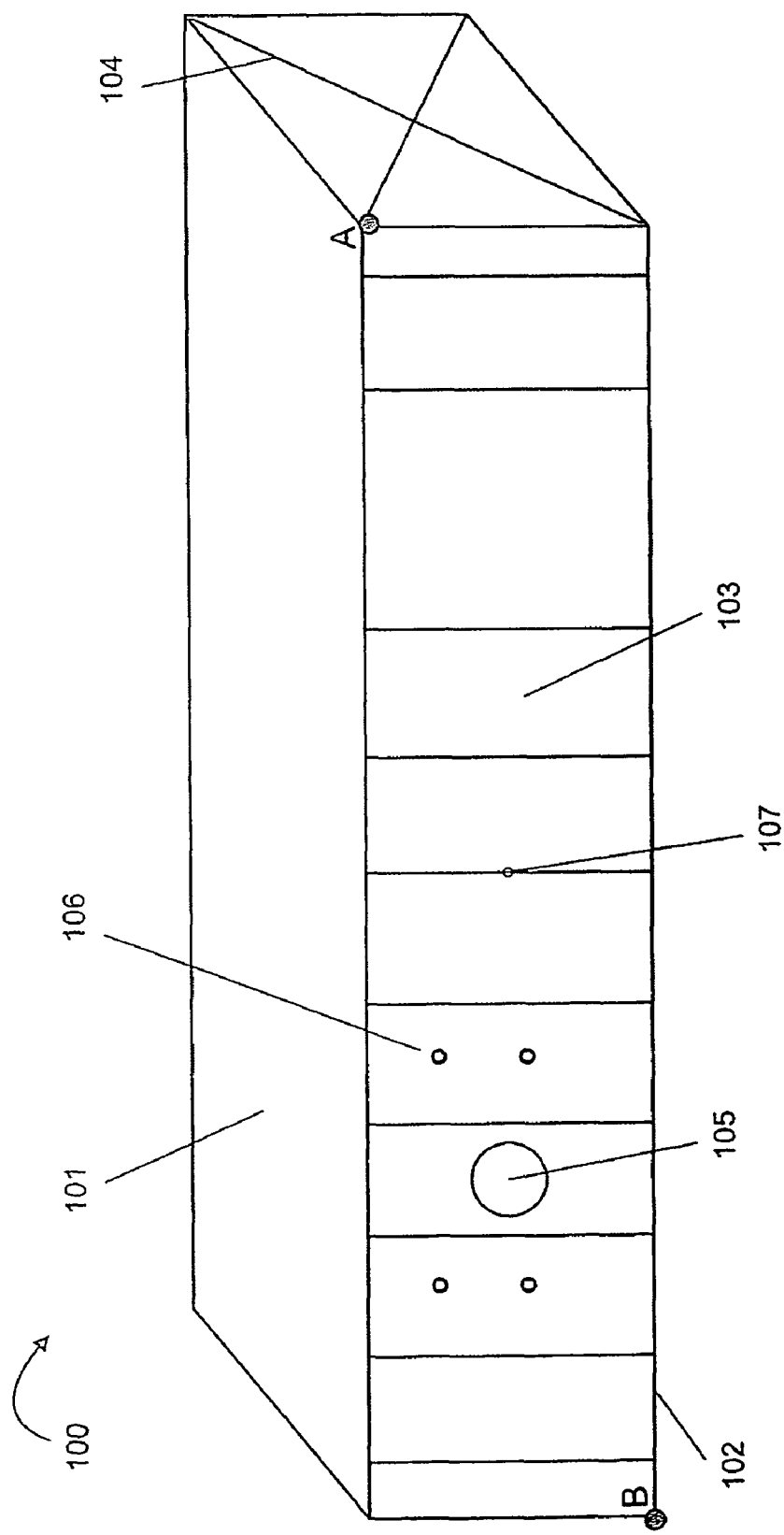
FIG. 1 is a front schematic view of the front spar of an aircraft wing between the fuselage and the first engine with acoustic emission sensors attached.

One aspect of the present invention provides a method and system for building a model of the effect of acoustic paths in a structure. The model is built by inducing a plurality of types of acoustic emissions at many positions in the structure and by detecting the acoustic emissions using a plurality of acoustic emission sensors that are arranged on the structure.

In this aspect, the model takes into account inhomogeneities of the structure, as well as differences in acoustic propagation modes in the structure, so that errors in the location of the damage sites can be reduced.

The model can store any of differences in times of arrival of the acoustic emissions at the sensors, wave-shape information, emission durations, amplitudes of the acoustic emissions and rise times of the acoustic emissions. The model also stores position information, which can be for example information on x, y and z coordinates (or coordinates in any other convenient coordinate system) for a three dimensional structure, for respective acoustic emission data for positions. The model can also store different information for different types of acoustic emissions corresponding to different types of damage.

In one embodiment, the process for determining the model involves an optimisation process whereby it is determined whether all of the positions can be uniquely identified i.e. whether acoustic emissions are received at three or more sensors to allow triangulation. If not, the optimisation process involves moving a sensor to a position not uniquely identified or placing a new sensor at such a position. Once an array of sensors is determined that enables all positions to be uniquely identified, an optimisation algorithm can be used to determine the optimum number and positions for the sensors.

In one embodiment of the invention, the model can be supplemented or adapted by the addition of data obtained during use of the model. Additional model data can be obtained from additional positions, which are interspersed between the original model positions by inducing acoustic emissions at these additional positions, and detecting and processing the emissions.

In another aspect of the invention the model characterising the effect of acoustic paths is incorporated in a method and system for locating a site of structural damage, for example cracking, fretting or rubbing in a structure in order to reduce errors in the location of acoustic emissions, and thus the location of the site of structural damage compared with the prior art methods which assume structural homogeneity. Acoustic emissions are detected from the site of structural damage at several acoustic emission sensors arranged on the structure. A data processing system is used to process the detected acoustic emissions using the model characterising the effects of the acoustic paths. The model includes data identifying different types of acoustic emissions and corresponding types of structural damage, and the data processing system locates and identifies structural damage using the model data. As the model takes account of the non-uniformity of acoustic paths caused by structural inhomogeneities, errors in the determined location of the site of structural damage can be reduced compared to the prior art method.

Another aspect of the invention provides a system and method for correlating structural damage to a structure, as indicated by acoustic emission data detected by sensors placed in the structure, with modes of structure use that caused the damage. This aspect of the present invention can be used in any structure, such as a static structure e.g. a bridge or oil rig, or moving machinery such as a motorised stationary machine or a vehicle. The invention has particular application for detecting damage in vehicle structures such as aircraft and correlating the damage with causal modes of vehicle operation. Results of the correlation can be output and presented in a form that is useful to operators such as pilots or drivers and maintenance personnel either during operation or after operation. The system can provide in-flight information to pilots relating to them that at a particular time they were performing a manoeuvre structural damage was caused at a particular location in the aircraft structure. This system and method can also be used with a model characterising acoustic paths, which reduces errors associated with inhomogeneities in the vehicle structure.

A system and method for confirming a site of structural damage in a structure using an acoustic emission source is provided in another aspect of the invention. The acoustic emission source is used to induce acoustic emissions at the site of damage, which has already been detected using fixed location sensors to detect acoustic emissions emitted by the damage. The induced acoustic emissions are received by the sensors and the acoustic emission source is moved until the induced acoustic emissions are substantially concurrent with the acoustic emissions originally detected from the damage. This indicates that the acoustic emission source has confirmed the site of damage.

In one embodiment of this aspect of the invention, the detected acoustic emissions can be processed using a model characterising acoustic paths to further improve the results confirming where in the structure the damage is located.

In one embodiment of this aspect of the invention, the acoustic emission source can be adapted to emit different types of acoustic emission, by for example varying the frequency, duration, amplitude and/or rise time of the acoustic waves emitted by the source. Each type of damage has an acoustic emission signature, comprising details such as wave-shape, frequency, duration, amplitude and rise time. The signatures are unique to each type of damage so damage can be characterised by simulating its corresponding acoustic emission signal using the source in the region of the damage and comparing the detected acoustic emissions from the source with the acoustic emissions detected from the structural damage.

In one embodiment, to provide operator feedback, an audible or visible output is generated dependant upon the proximity of the two detected positions in order to guide the operator to move the source to the site of structural damage.

Another aspect of the present invention provides a system and method for simulating acoustic emissions generated from structural damage in a structure. A set of acoustic emission data from a plurality of regions of structural damage is acquired to obtain a set of acoustic emission signatures associated with each of the plurality of regions. An acoustic emission source is then adapted to emit each acoustic emission signature. Thus in this aspect an acoustic emission source can be tuned to emit the required signature to simulate damage.

A further aspect of the present invention provides a system and method for verifying structural damage in a region of interest in a structure, the damage having been recorded in a database for a plurality of locations. The system and method comprises inducing acoustic emissions in the region of interest in the structure using an acoustic emission source; detecting the acoustic emissions induced at the region of interest; identifying the location of the region using the detected acoustic emissions; and determining all recorded locations of damage recorded in the database using the identified location of the region.

A further aspect of the present invention provides a system and method for correlating a site of structural damage in a structure with causal modes of structural operation or use. The system and method comprises detecting acoustic emissions from the site of structural damage in a structure at a plurality of acoustic sensors arranged in the structure; processing the detected acoustic emissions to locate the structural damage; acquiring structural operating parameters from the structure; processing the structural operating parameters to determine the mode of structure use; correlating the structural damage with the determined mode of structure use to determine a causal mode of structure use; recording the site of structural damage as a first position and the determined causal mode of structure use; inducing acoustic emissions at a second position in a region of the first position in the structure using an acoustic emission source; receiving the acoustic emissions induced at the second position; determining the second position using the received acoustic emissions; moving the acoustic emission source until the determined second position is substantially concurrent with the first position in the structure to confirm the location of the structural damage; and outputting information on the confirmed location of the structural damage and determined causal mode of structure use.

Another aspect of the present invention provides a method and system for determining a site of structural damage in a structure. A plurality of acoustic sensors detect acoustic emissions from the site of structural damage on the structure. A data processing system processes the detected acoustic emissions using a model characterising effects of acoustic paths between a plurality of predetermined positions on the structure and the acoustic sensors to determine a first approximate position of the structural damage, wherein the first predetermined position lies on one of the predetermined positions. An acoustic emission source induces acoustic emissions at a second position in a region of said first position in the structure. The sensors detect the acoustic emissions induced at the second position. The data processing means processes the detected acoustic emissions using the model to determine the second position using the received acoustic emissions, and compares the processed acoustic emissions from the structural damage with the processed acoustic emissions from the acoustic emission source to determine if the second position is the site of structural damage.

In one embodiment of this aspect of the invention, if the comparison does not determine that the second position is the site of structural damage, the acoustic emission source is repeatedly moving and the inducing, detecting and processing steps are repeated to determine the second position until the second position is determined to be the site of structural damage.

In one embodiment, a direction to move the acoustic emission source is determined using the model. A direction indicator can output to an operator to assist in the location of the site of structural damage.

In another aspect of the invention there is provided apparatus (such as a hand held, optionally self-powered device) for simulating acoustic emissions, comprising: input means (such as one or more switches, buttons or other electrical and/or physical input devices) for inputting a selection of one of a plurality of types of structural damage (such as cracking, fretting, and so on); and an inducing arrangement for inducing acoustic emissions corresponding to the selected type of structural damage. The apparatus may further comprise storage means (such as a flash memory, hard disk or other read-only or random access storage device) for storing acoustic emission data (such as a characteristic acoustic emission signature) corresponding to the plurality of types of structural damage; and processing means (such as a processor and associated memory, or an ASIC, for example) for selecting stored data corresponding to the selected type of structural damage and operating the inducing arrangement in accordance with the selected data. This apparatus and/or its method of use may form part of any of the abovementioned systems and methods respectively. For example, the apparatus may be in communication (by a wireless or other link) with other devices, such as computers operating modelling or acoustic emission detection processes, in order to share and receive data relating to simulated acoustic emissions. Although the present invention can be used on any structure, it has been found to be particularly useful when used for detecting structural damage on aircraft structures, where structural failures can be catastrophic. It has been found that damage such as cracking occurs at points of stress on an aircraft.

Referring now to FIG. 1, this shows a schematic diagram of an arrangement for locating a site of damage on a typical aircraft structure by detecting acoustic emissions from the site of damage. The aircraft wing has an upper spar cap 101, a lower spar cap 102, a front spar 103, and cross-sectional stiffeners 104. The front spar 103 has reinforcing ribs 107 running vertically at spaced intervals. A fuel aperture 105 is provided on the inside of the front spar 100 and acoustic emission sensors 106 are acoustically coupled to the front spar 103 at several positions.

The illustrated part of the wing 100 is the section of the aircraft wing between the aircraft fuselage and the first engine. The vertical strut 103 supports the upper spar cap 101 and the lower spar cap 102 and the cross-sectional stiffeners 104 add stiffness to the structure of the wing and provide added strength to the front spar 103. The acoustic emission sensors 106 detect acoustic emissions originating from the source of damage on the front spar 103. The acoustic emission sensors are piezoelectric transducers with a resonant frequency in the range of the resonant frequency of the structure under investigation. In aluminium structures, transducers with resonant frequencies of around 200-300 kHz are suitable. The sensors 106 are attached to the structure of the front spar 103 by means of cable ties and self-adhesive bases. In addition, a sealant is used as a joining compound between the base of the sensor and the structure in order to provide a low attenuation acoustic coupling.

Differences in the time of arrival (Δt) of features, such as the leading edges of acoustic emission signals from sources of damage on the structure of the front spar 103 at the sensors 106 or the times of the peak signals from each sensor are used by a triangulation algorithm in analysis software to locate the source of the acoustic emission and therefore the damage. Although the surfaces of modern aircraft structures tend to be substantially homogeneous, discontinuities in the structure result from components in the interior of the structures, for example the vertical struts 103, the cross-sectional stiffeners 104 and the fuel aperture 105. Older aircraft also have surface discontinuities, since their structures consist primarily of riveted and bolted extruded or machined aluminium sections and plates.

For example, the discontinuities and inhomogeneities in the structure of the front spar 100 will cause an acoustic path from point A to point B shown in FIG. 1 to be non-uniform, as the acoustic transmission speed will change as it propagates through the structure. This leads to errors in Δt in the triangulation algorithm, which in turn leads to errors in the location of the site of damage on the aircraft structure.

Figure 2:
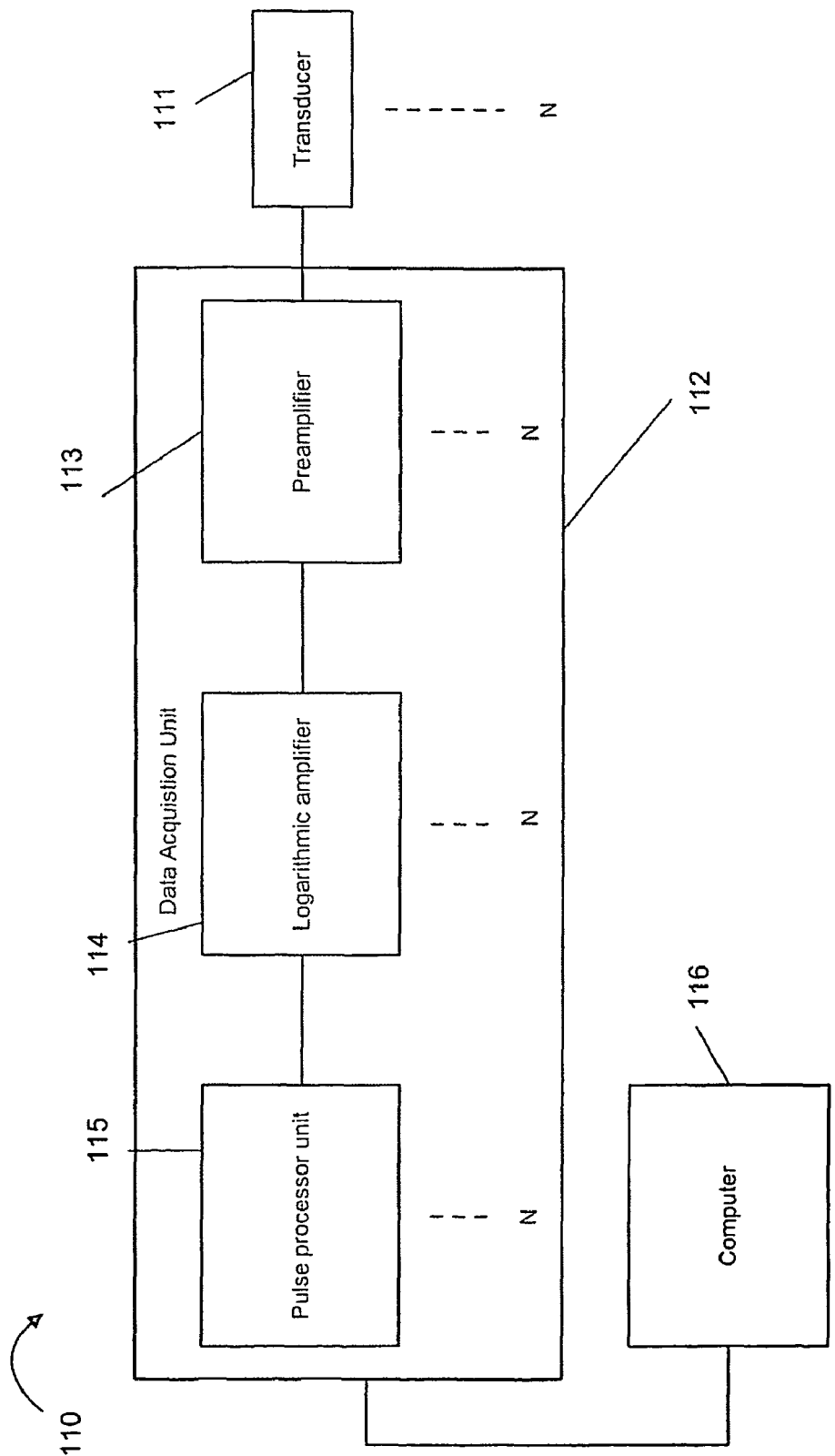
FIG. 2 is a schematic diagram of data acquisition and processing system of the prior art.

A schematic diagram of a system 110 for detecting and acquiring acoustic emission data from a structure is shown in FIG. 2. This system is known in the art and a similar system is described in US 2003/0140701. A sensor 111 is coupled to a preamplifier 113, which is connected to a data acquisition unit 112. The data acquisition unit 112 comprises a logarithmic amplifier 114 and a pulse processor unit 115. The data acquisition unit 112 is connected to a computer 116.

Acoustic emissions from sites of damage on the structure are detected by sensors 111, which comprise the acoustic emission sensors 106 placed on an aircraft structure as shown in FIG. 1. The sensors 111 are acoustically coupled to the aircraft structure and can be, for example, a piezoelectric sensor with a resonant frequency in the range from 20 kHz to 2 MHz. Any damage such as cracking on an aircraft structure will emit acoustic waves with a fundamental frequency equal to the resonant frequency of the structures. The resonant frequency of the sensor should therefore be the same as that of the structure being investigated. Typically aluminium aircraft structures have a resonant frequency in the region of 300 kHz, so this is the preferred frequency of sensor to use for detecting acoustic emissions from an aircraft structure. In practice the sensors generally have a bandwidth of a few hundred kHz and sample acoustic data at 15 MHz.

The preamplifier 112 is located in the vicinity of the sensor. There is an array of sensors and preamplifiers having N channels, each channel having one sensor 111 and one preamplifier 113. When calculating the Δt values of acoustic emissions, at least three sensors are required for triangulation. The sensors are acoustically coupled to the structure in spaced apart locations. Each sensor 111 is connected to the data acquisition unit 112 for acquiring and processing acoustic emission data from acoustic emission pulses.

The sensors 111 and preamplifiers 113 are connected to the data acquisition unit 112. The distance between the sensors 111 and the data acquisition unit 112 is installation dependant. In practice, when detection of acoustic emissions takes place from an aircraft structure, the data acquisition unit 112 is located within the avionics bay of the aircraft and is powered from the aircraft's power supply.

There will be background noise from sources such as the aircraft engines that will interfere with acoustic emission signals from the aircraft structure. The data acquisition unit 112 conditions the acoustic emission signals received at the sensor 111 and performs real time filtering and signal processing to isolate acoustic emissions from background noise and produce acoustic emission data that can be used to locate a source of damage on the aircraft structure. The signal received at the sensor takes the form of a wave packet. In each channel the logarithmic amplifier 114 rectifies the signal received from the preamplifier 112. The rectified signal then enters the pulse processor unit 115, which converts the acoustic emission signals received at the sensor 111 to digital signals, filters the digital signals and isolates the digital signals in order to distinguish acoustic emissions received from damage on the structure from background noise.

The digital signals from each channel take the form of pulses, which are analysed by a computer 116 using a triangulation algorithm. Each sensor 111 is generally at a different distance from the site of damage, which means that acoustic emission signals from the damage will reach each sensor at a different time. The location of the damage can be identified by measuring the difference in times of arrival between sensors (Δt) and using acoustic velocity information for each sensor 111. This process is known as triangulation. However, triangulation assumes a homogeneous structure and a uniform speed of sound in all directions in the structure, so there will be errors in the location of the damage as calculated by this method. Therefore, this method of locating damage may not provide the exact location of the damage.

Figure 3:
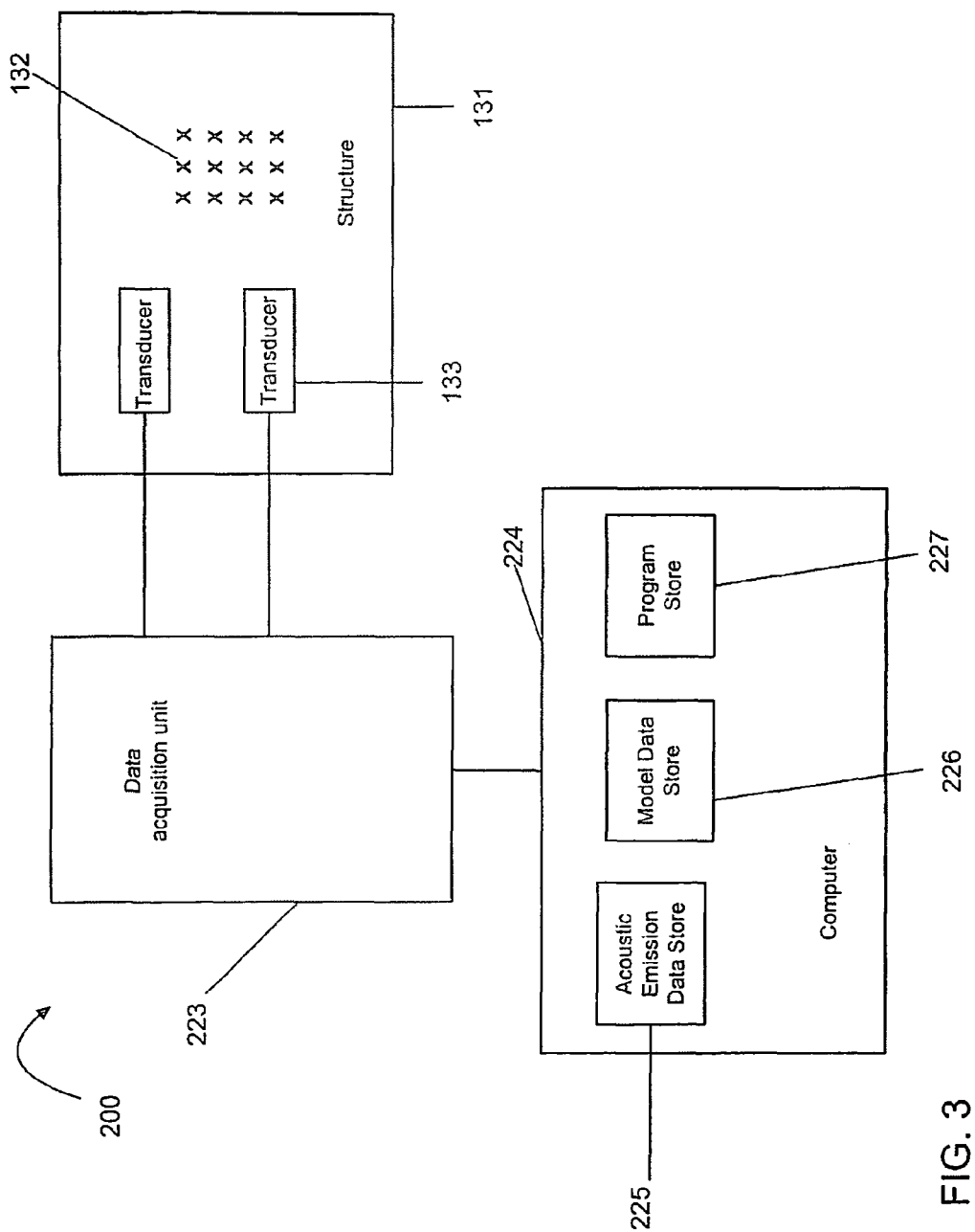
FIG. 3 is a schematic diagram of the apparatus used to build a model of acoustic paths in a structure according to a first embodiment of the invention.

An improvement on the known system involves incorporating a model of acoustic paths into the system for locating damage. A first embodiment comprising a method and system for building a model of acoustic paths will now be described with reference to FIGS. 3, 4, 5A and 5B. FIG. 3 shows apparatus 200 used for building a model of acoustic paths. Acoustic emissions are induced at positions 132 in a structure 131. Sensors 133 are acoustically coupled to the structure 131 and connected to a data acquisition unit 223. The sensors 133 and data acquisition unit 223 are of the same configuration as those shown in FIG. 2 and the data acquisition 223 unit comprises the same components as the data acquisition unit 112 shown in FIG. 2. The data acquisition unit 223 is connected to a computer 224 comprising an acoustic emission data store 225, a model data store 226 and a program store 227.

Figure 4:
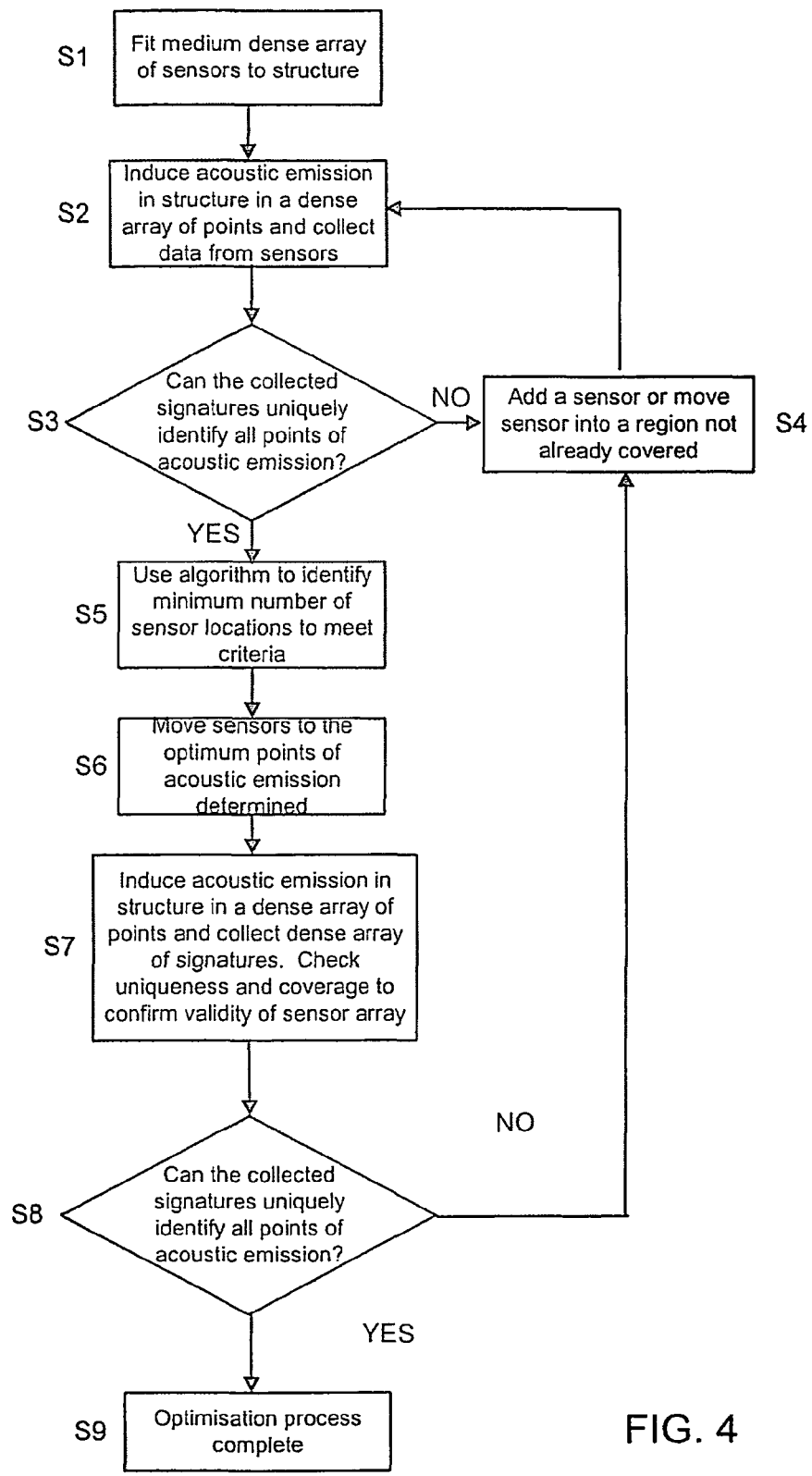
FIG. 4 is a flow diagram of the process used to build a model of acoustic paths in a structure according to the first embodiment of the invention.
Figure 5A:
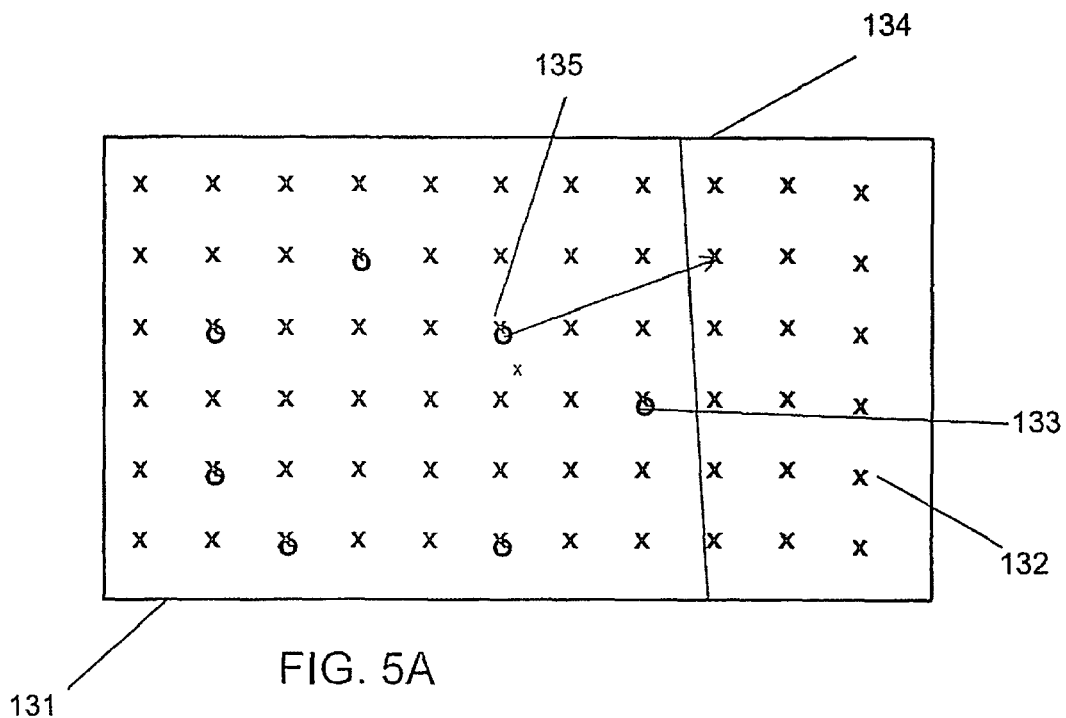
FIGS. 5A and 5B are schematic views of points at which acoustic emission is induced in a structure for building a model of acoustic paths in the structure.
Figure 5B:
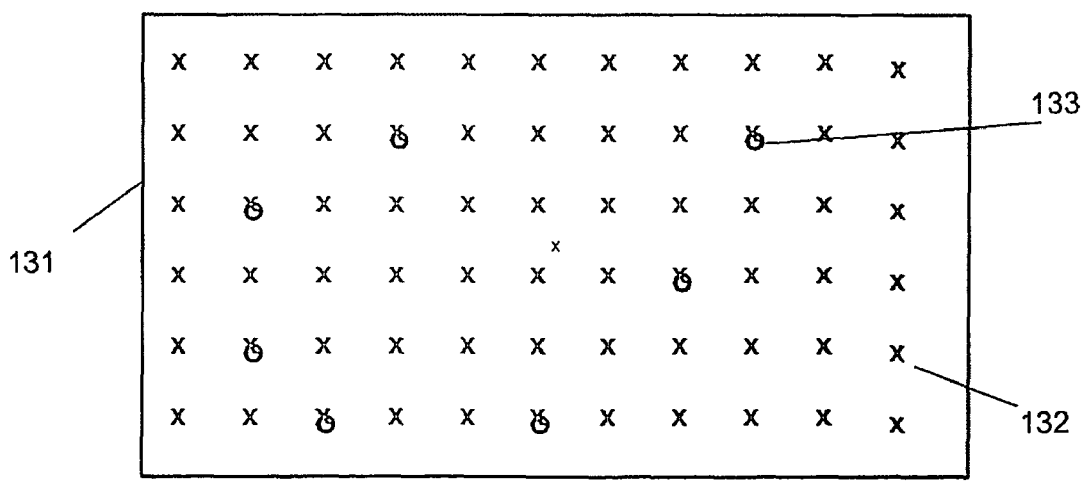

FIG. 4 is a flow diagram showing the steps involved in building the model and FIGS. 5A and 5B are schematic diagrams of points in a structure at which acoustic emissions are induced and detected to build the model of acoustic paths.

In step S1 of FIG. 4 a medium dense array of sensors is fitted to the structure. This is illustrated in FIG. 5A, where an array of sensors 133 is acoustically coupled to the surface of a structure 131. The structure 131 can be the aircraft wing front spar 100 shown in FIG. 1. This initial arrangement can be chosen based on an informed guess or based on information from the aircraft manufacturer on the acoustic properties of the aircraft. In step S2 of FIG. 4 acoustic emissions are induced at a grid or array of positions 132 in the structure so that positions 132 have acoustic emission signatures associated with them. The spacing or density of the positions can be selected as appropriate. The greater the density of the positions; i.e., the more closely they are spaced, the more accurate the damage position location will be. However, a close spacing of positions of induced acoustic emissions leads to a greater computation requirement so an appropriate spacing of around 10 cm between each point is used in this example. The positions of the sensors 133 on the structure 131 is the same as the positions on the structure where acoustic emissions are induced; i.e., sensors are placed at positions on the grid. However, the number of sensors 133 in the array can be considerably less than the number of points 132. In a preferred embodiment acoustic emissions are induced at a dense array of points in a grid pattern. The acoustic emissions can be induced by a Hsu-Neilson source (snapping a 2H pencil lead against the structure) or by a source adapted to emit frequencies equal to a resonant frequency of the structure. The acoustic emissions are most practically generated by moving the source sequentially to the positions. However, multiple sources can be used for sequential emissions at any number of the positions.

The acoustic emission signatures from points 132 are detected by the sensors 133 and acoustic emission data is collected and processed by the data acquisition unit 223 shown in FIG. 3, which comprises the apparatus shown in FIG. 2 and described above. Acoustic paths are considered reciprocal i.e. the time taken for an acoustic wave to travel between positions is the same in both directions. The reciprocity of acoustic paths is used to determine at which points on the structure to put sensors so they are able to uniquely identify acoustic emissions from damage at any point on the structure. If the locations of the sensors 133 and the locations of the positions 132 are then reversed, it follows that the sensors when placed in the locations of the points 132 will be able to uniquely identify acoustic emissions from any point on the structure. This means that all positions 132 are potential source locations. If all positions can be uniquely identified, an optimisation algorithm can be used to determine whether any sensors 133 can be moved or removed.

In step S3 it is determined whether the acoustic emission signatures collected by the sensors 133 can uniquely identify all positions 132 of acoustic emission. If it is determined that all points of acoustic emission can be uniquely identified, at step S5 the optimum positions to place the minimum possible number of sensors can be found by an optimisation process. A database representing a three-dimensional map of acoustic paths between the points 132 and the sensors 133 is obtained. This can be achieved by using a triangulation algorithm to obtain the $\Delta t$ values from all points 132 to all sensors 133. The best configuration on the structure for the array of sensors and minimum number of sensors to meet the criteria; i.e., to uniquely identify all locations of structural damage is then found by methods well-known in the art, for example as genetic algorithms or simulated annealing.

The determined minimum number of sensors 133 are then moved to their new positions, which are the optimum determined points 132 (step S6). A verification process (step S7) then takes place to check that the sensors in the optimum determined positions can uniquely identify all positions of acoustic emission on the structure that are required to be detected. Acoustic emission is induced by acoustic emission sources at a dense array of positions 132 on the structure and the acoustic emission signatures from the points are collected by the sensors 133. If the sensors 133 can uniquely identify the acoustic emission signatures from all areas of the structure that are required to be detected (step S8), then the optimised model is valid and the optimisation process is complete. However, if acoustic emission signatures from all areas of the structure that are required to be detected cannot be uniquely identified, then the process must return to step S2 and carry out steps S2 to S6 until the collected signatures can uniquely identify all positions of acoustic emission. This is determined at S8 by analysing data stored in the acoustic emission data store 225 using analysis software in the program store 227. If at S8 the position of the sensors for uniquely identifying all positions of acoustic emission, then model data defining the acoustic path data is stored in the model data store 226. Model data includes $\Delta t$ values for acoustic paths between all positions 132 and wave-shape information. The model data store 226 can comprise model data from different sources of acoustic emission, corresponding to different types of damage such as cracking, delamination, fretting and rubbing.

The acoustic emissions are detected by the sensors 222, where they are filtered and processed by pre-amplifiers, logarithmic amplifiers and pulse processor units in the data acquisition unit 223 to obtain acoustic emission data, which is then stored in the acoustic emission data store 225 located in the computer 224. The apparatus for filtering and processing acoustic emissions is shown in FIG. 2. Analysis software in the program store 227 then analyses the acoustic emission data stored in the acoustic emission data store 225 to determine whether all positions can be uniquely identified (step S3 and step S8).

If the sensors 133 cannot uniquely identify all positions 132 then a sensor is added or moved from a region of the structure that is already well covered by sensors to a region 134 that is more sparsely covered, as shown in FIGS. 5A and 5B and step S3 in FIG. 3. Steps S2, S3 and S4 should be repeated until the sensors can uniquely identify all positions 132. When all points 132 on the structure have been uniquely identified and the sensors 133 are placed in the positions where they can uniquely identify the points, the model is complete at step S3. However, it is desirable for reasons of cost and practicality to use the minimum number of sensors possible for uniquely identifying acoustic emissions and to place them in the optimum positions for maximum coverage of the structure.

The model data obtained using this technique can include differences in times of arrival of the acoustic emissions, duration, wave-shape information such as amplitude, and power for each path from a position and also for multiple signatures i.e. multiple emission sources simulating multiple types of damage. The model thus models the effect of the acoustic paths on the emissions generated by the structural damage i.e. the way the acoustic paths delay the emissions and change their wave-shape.

In order to build the model to include signatures for different types of damage for each position, the acoustic emission source needs to be able to simulate the acoustic emissions of various types of damage. In one embodiment of the invention, the acoustic emission source can be adapted to do this by a method of detecting a signature that has come from a known type of damage at a known location (the determination of the location may require inspection subsequent to the occurrence of the damage, or the location method of the second embodiment of the present invention could be used). The wave-shape information can thus be recorded for the damage and the acoustic emission source can be adapted e.g. iteratively until is generates an acoustic emission signature that matches. This method can be repeated for a plurality of known types of damage at a plurality of locations to enable a library of emission characteristics necessary for the emission source to generate signatures that simulate damage at a region. The emission source can then be used to generate different signatures at each position to populate the model with path information for different acoustic signature.

Figure 6:
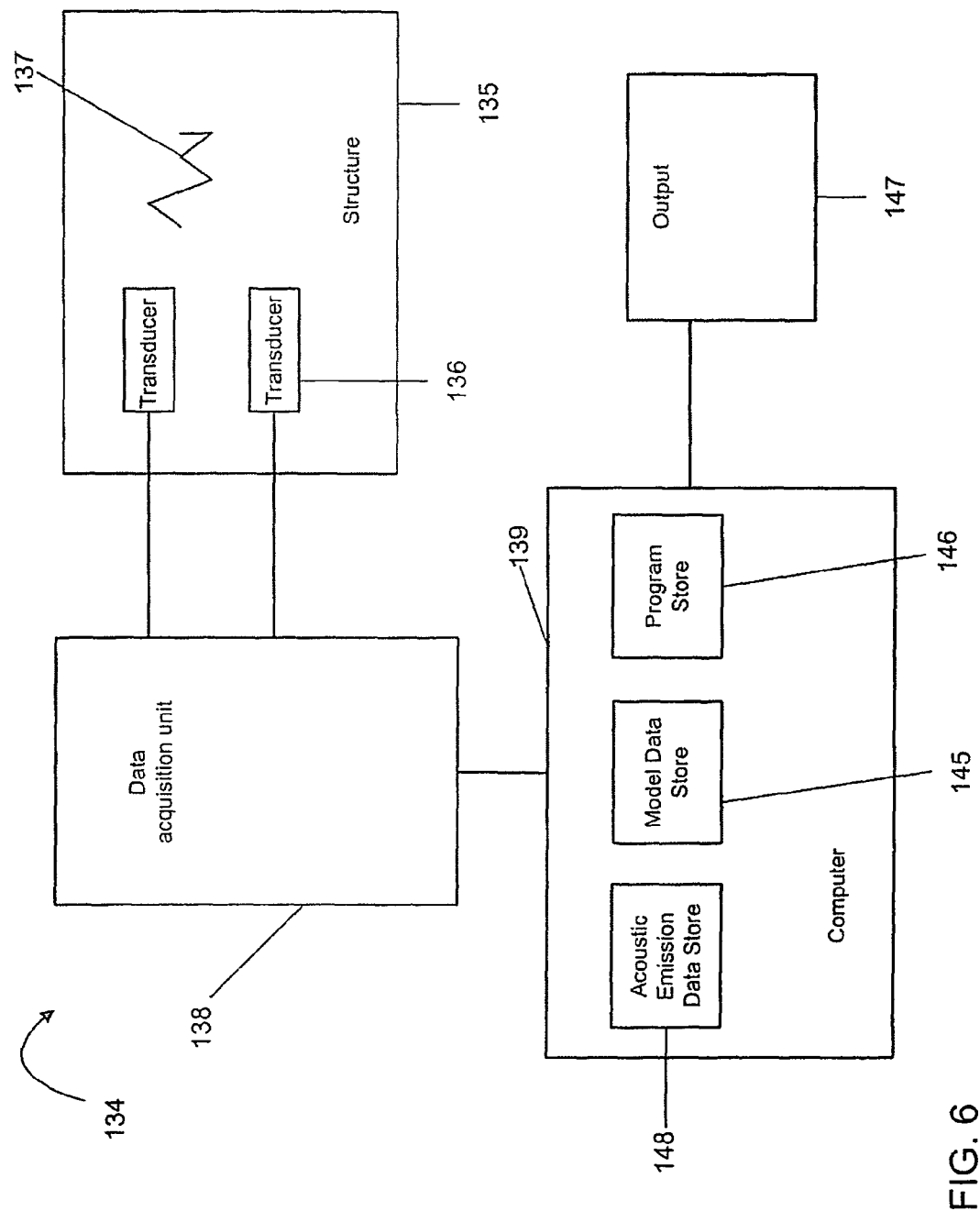
FIG. 6 is a schematic diagram of an acoustic integrity monitoring system according to a second embodiment of the present invention.

The model of acoustic paths can be used to find the location of structural damage in a structure. A second embodiment for locating emissions from the sites of structural damage will now be described with reference to FIGS. 6 and 7. FIG. 6 shows a system 134 for locating a site of structural damage in a structure. An array of sensors 136 is acoustically coupled to a structure 135, in which damage 137 is to be monitored. The sensors 136 are connected to a data acquisition unit 138 that is connected to a computer 139. The computer 139 includes an acoustic emission data store 148, a model data store 145 and a program store 146. The sensors 136 are used as acoustic emission sensors to detect acoustic emissions from the damage 137 in the structure 135. Acoustic emissions detected by the sensors 136 are filtered and processed by the data acquisition unit 138 to obtain acoustic emission data. The data acquisition unit 136 comprises the same filtering and processing components as the data acquisition unit 112 shown in FIG. 2. Each acoustic emission that takes place in the structure 135 has a Δt value associated with it for each sensor from the array of sensors 136 that detects it, as well as an amplitude, duration and a rise time. Acoustic waveforms detected at the sensors 136 are received by the data acquisition unit 138, which logs the time of arrival of the leading edge of the waveforms received at the sensors 136 and filters out waveforms not having the characteristic acoustic emission frequency of the structure. This results in a set of acoustic emission data that has undergone a first stage of filtering and is stored in the acoustic emission data store 148 located in the computer 139. The difference between times of arrival of the acoustic waveforms at the sensors 136, Δt is calculated using an algorithm stored in the program store 146. A matrix of acoustic emission data including Δt values, amplitudes, durations and rise times is then accumulated in the acoustic emission data store 148 for each acoustic signature; i.e., the acoustic waveform received at each of the sensors 136 from each point of acoustic emission in the structure 135. Every time an acoustic event with a certain Δt value, amplitude, duration and rise time occurs, it is logged as an event at a point on the matrix associated with that particular Δt value, amplitude, duration and rise time. Each point on the matrix will have a Δt value, amplitude, duration and rise time associated with it for every sensor in the array 136. Points on the matrix having many logged events will correspond to regions of structural damage, as they indicate many acoustic emissions with the same Δt values, amplitude, duration and rise time are occurring in the same region of the structure. The accumulation uses Δt values to plot regions of damage according to the differences in times of arrival of the events. The accumulation process allows for the aggregation of events by Δt values until a threshold is reached at which point it is considered that damage has occurred. The model is used to map the Δt values for the accumulated data to positions on the structure by comparing the Δt values with the Δt values stored in the model.

As an alternative method for processing the acoustic emission data, instead of accumulating the Δt values in order to identify significant events relating to the occurrence of damage and the mapping the Δt values for the accumulated data to position coordinates using the model, Δt values for each detected event can be mapped to position coordinates using the model and the events can be accumulated in spatial coordinates to determine significant events. This has the advantage of reducing errors in the spatial location of individual events but brings with it a higher processing overhead.

There are at least three sensors in the array 136 but in practice the number of sensors is usually considerably greater. Therefore each point on the matrix may have many Δt values associated with it, which could result in a very large accumulated data set that would require a great deal of memory to be used at the acoustic emission data store 148. To reduce the amount of data that is required to be stored in the acoustic emission data store 148, a threshold value is set for the number of events occurring at each point on the matrix. Only when the threshold value is reached are the Δt values, amplitude and rise time recorded for the event for the threshold event in the acoustic emission data store 148. The previous events below the threshold value are disregarded. The matrix is then cleared, stored in a secondary matrix and then built again until the required set of acoustic emission data is acquired. An alternative method of reducing the amount of recorded data is to narrow down the area of the matrix, as there are likely to many acoustic events occurring in a small area of the matrix corresponding to a localised area of structural damage.

This method gives an indication of the region on the structure in which there is structural damage. However, as previously discussed there are errors in the location of the position of structural damage at this stage, due to inhomogeneities in the structure leading to triangulation errors when calculating Δt values. The acoustic emission data stored in the acoustic emission data store 148 is then mapped onto model data obtained from the model of acoustic paths in the previous embodiment that is stored in the model data store 145. In the model of acoustic paths, the sensors are placed on the points of acoustic emission found using the reciprocity of acoustic paths. Therefore, when the acoustic emission data is mapped onto the model data, the points of acoustic emission originating from structural damage can be located without triangulation errors, as the inhomogeneity of the acoustic paths has already been taken into account.

Figure 7:
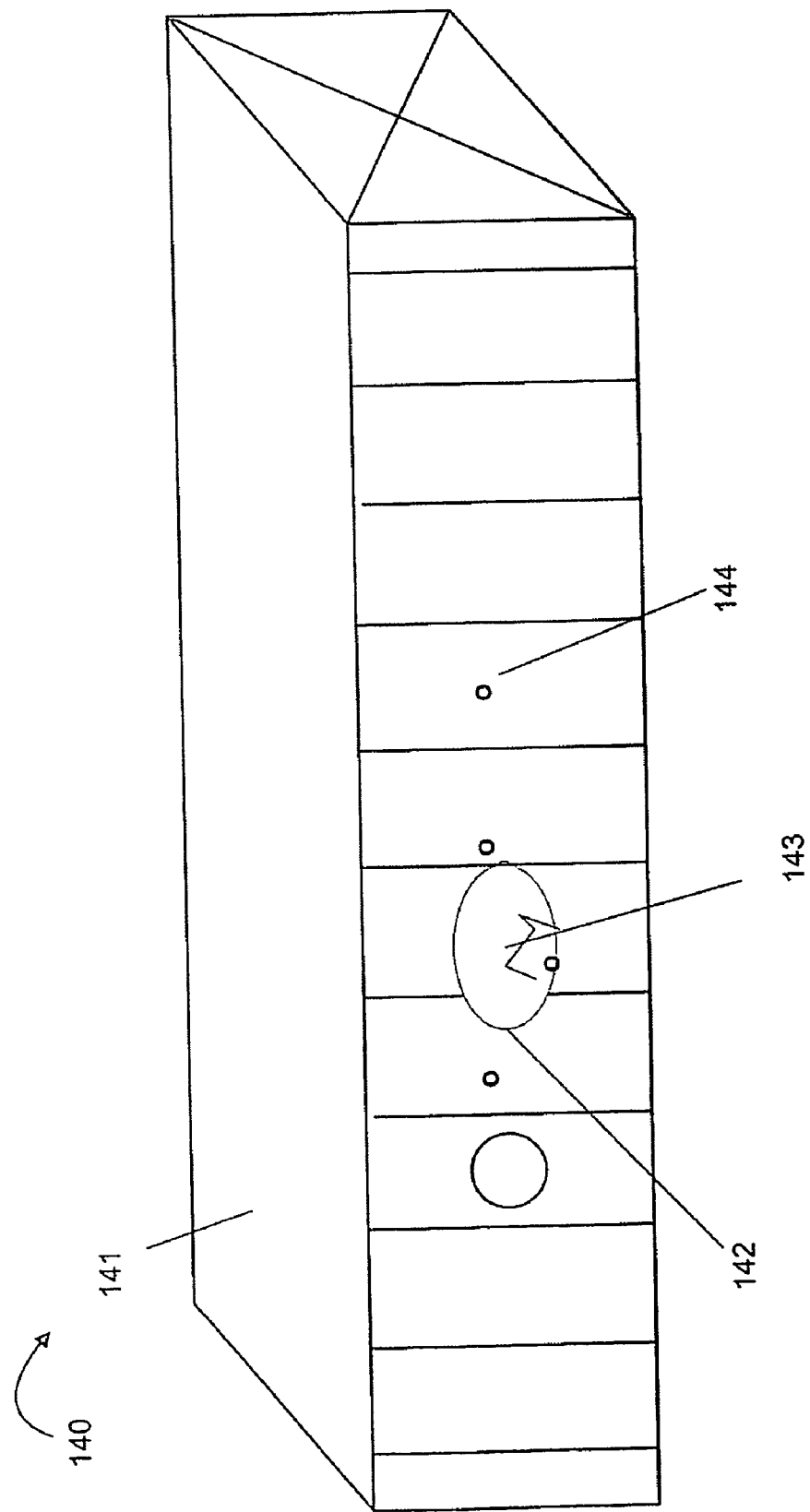
FIG. 7 is a schematic diagram of the front spar of an aircraft wing with acoustic emissions sensors acoustically coupled to detect damage.

An example of how the system for locating a site of structural damage in a structure could be used is shown in FIG. 7. Sensors 144 are acoustically coupled to a front spar cap 141 of the front spar of an aircraft wing 140 around a hole 142 in the front spar cap into which a crack 143 is spreading. The sensors 144 detect acoustic emissions originating from the crack 143. Acoustic emission data acquired from the crack 143 can then be mapped using the model of acoustic paths to locate the site of the crack. Even though the crack is inside the hole 142, the site of the crack can be located because the model of acoustic paths is three-dimensional and works for acoustic emissions originating from any point in a structure.

The above-described method and system of detecting structural damage can be used to provide a method and system for correlating structural damage with causal modes of structural operation or use. A mode of structural operation or use is defined as a manoeuvre being performed by or on a structure in accordance with a set of operational parameters associated with the structure. For example, when applied to an aircraft, the operational parameters can include centre of gravity, acceleration, air speed, altitude, heading, aircraft location, pitch angle, roll angle, weight on wheels, flight surface positions, strain, temperature, and/or load. A mode of operation can be landing, pulling steeply out of a dive or a banking manoeuvre with high gravitational acceleration, for example.

Figure 8:
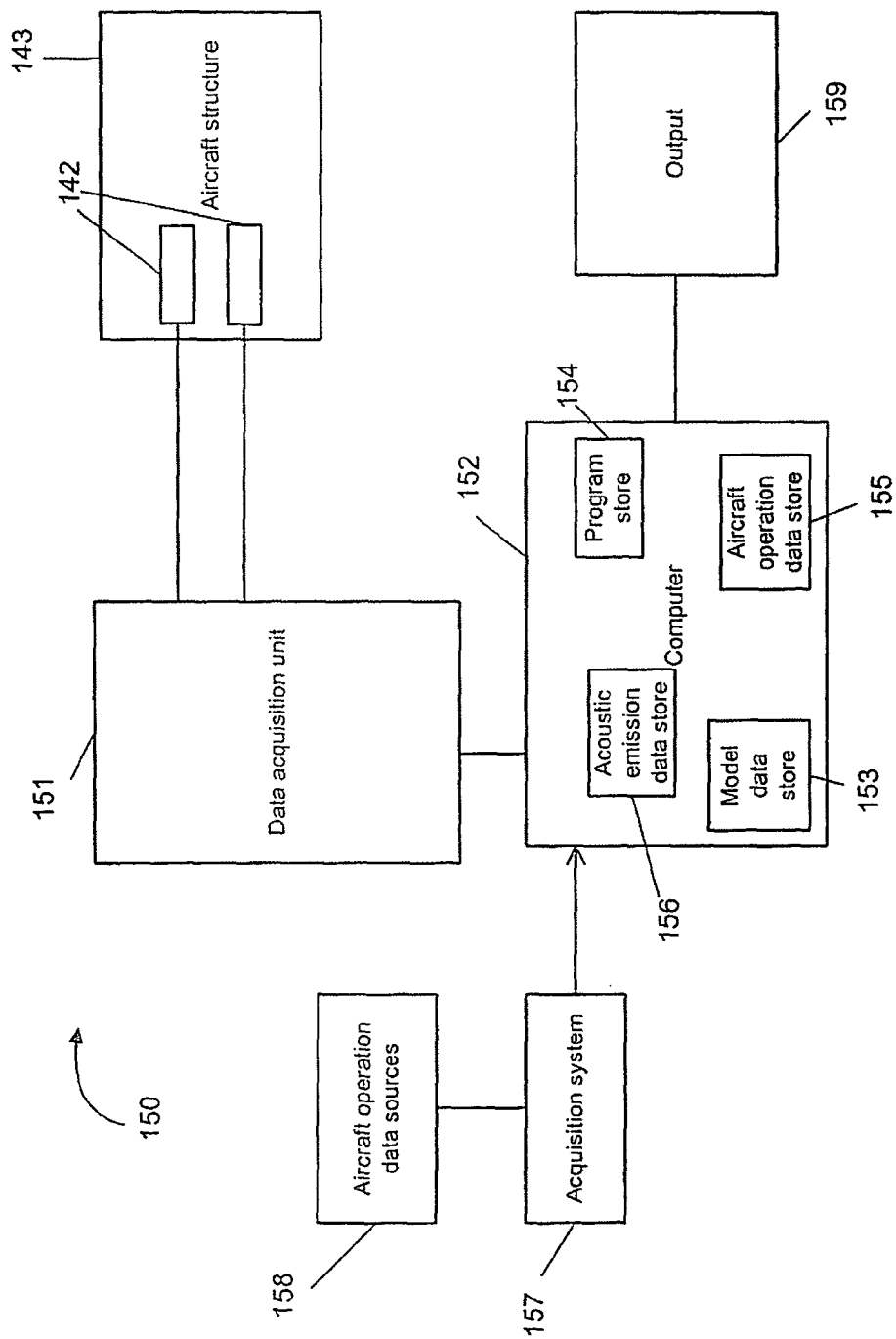
FIG. 8 is a schematic diagram of an acoustic integrity monitoring system for correlating structural damage to an aircraft with causal modes of aircraft operation according to a third embodiment of the present invention.

A third embodiment of the present invention will now be described with reference to FIGS. 8 and 9. FIG. 8 shows an apparatus 150 for correlating structural damage with causal modes of aircraft operation. An array of sensors 142 is acoustically coupled to the aircraft structure 143 and connected to a data acquisition unit 151, the components of which are shown in FIG. 2. The data acquisition unit 151 is connected to a computer 152, which comprises an acoustic emission data store 156, a model data store 153 for storing the model of acoustic paths built using the method shown in FIG. 3, a program store 154 and an aircraft operation data store 155. Aircraft operation data sources, for example strain gauges, are connected to a data acquisition system 157, which inputs data into the computer 152. An output 159, for example a display, outputs data from the computer 152.

Figure 9:
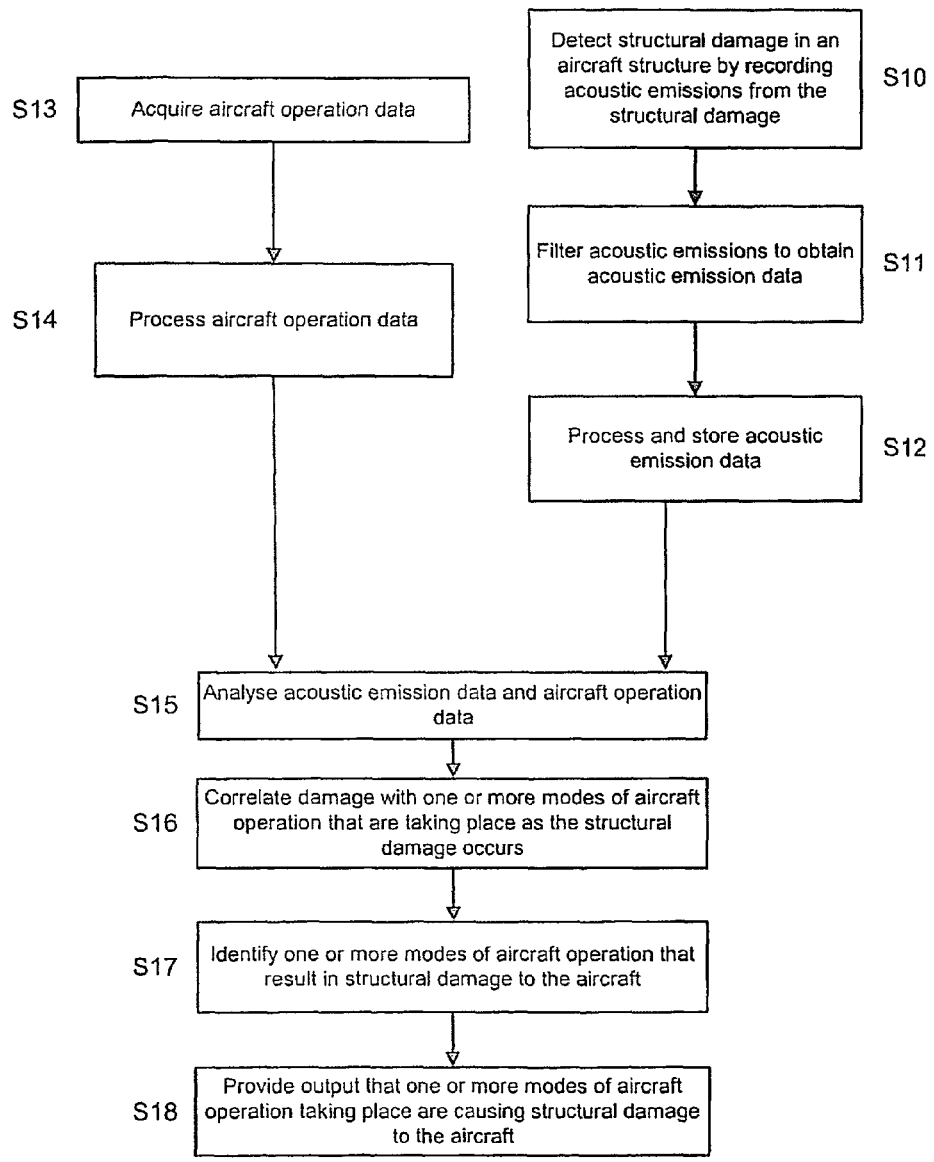
FIG. 9 is a flow diagram of a method for correlating structural damage to an aircraft with causal modes of aircraft operation.

FIG. 9 is a flow diagram of the process for correlating structural damage with causal modes of aircraft operation. Structural damage is detected (Step S10) in the aircraft structure by the sensors 142, which record acoustic emissions originating from the location of the structural damage. The acoustic emissions are then filtered (Step S11) to obtain acoustic emission data that is isolated from background noise on the aircraft. Filtering of the acoustic emissions is a two-stage process. First stage filtering is performed by signal processing apparatus in the data processing unit 151, which comprises the signal processing apparatus shown in FIG. 2. The signal processing apparatus selects certain Δt values and peak amplitudes that are normally associated with acoustic emissions from the acoustic waveforms received at the sensors 142 and filters out waveforms not having the characteristic acoustic emission frequency of the structure. Second stage filtering is performed by analysis software in the program store 154 by accumulating a spatial map of Δt values, amplitudes, durations and rise times of acoustic emission events for each waveform received at the sensors 142. Alternatively, filtering can take place by accumulating a spatial map of acoustic emission events, comprising information on □t values, amplitudes, durations and rise times of the waveforms, in the first instance, then frequency filtering an accumulation of Δt values rather than Δt values obtained from individual acoustic paths. When acoustic emission data has been obtained by filtering acoustic emission events, it is then mapped onto model data stored in the model data store 153 and stored (step SS123) in the acoustic emission data store 156.

Aircraft operation data is obtained from the aircraft operation data sources 158 and acquired at the acquisition system 157 (step S13). Aircraft operation data sources are sources of data about aircraft operation parameters and can be, for example, altimeters or strain gauges. The aircraft operation data is processed by the computer 152 and stored in the aircraft operation data store 155 (step S14). The aircraft operation data is obtained, acquired and processed in time synchronisation with the acquisition of acoustic emission data while the aircraft is in operation (step S15). The acoustic emission data from the acoustic emission data store 156 and aircraft operation data from the aircraft operation data store 155 is then analysed using analysis software stored in the program store 154 to correlate which of one or more modes of aircraft operation are taking place, determined from the aircraft operation data, as structural damage identified by the acoustic emission data is occurring (step S16). The correlation process produces a matrix of aircraft operation modes and related damage. One or more modes of aircraft operation are then identified as a cause of structural damage (step S117) and data is ten provided to the output 159 indicating that one or more modes of aircraft operation caused identified structural damage to the aircraft (step S18).

The present invention can be used on any structure but it works particularly well on aircraft, where structural damage caused by stress is potentially catastrophic. For example, the output 159, which can be visible or audible for example, can be used as to warn pilots during flight that they have just performed a manoeuvre with the aircraft that has caused structural damage and advise where the structural damage is located. Warning pilots could take place by adapting the output 159 to be a display panel for displaying information indicating the modes of aircraft operation taking place when structural damage occurred, the location of the structural damage and possibly the result of the damage on the aircraft's structure and/or performance. The pilot can then decide whether to modify his behaviour and change the mode of aircraft operation to contain the damage based on the warning. Alternatively, or in addition, there can also be a system provided for receiving the output 159 and preventing the pilot from performing the particular manoeuvre that caused identified structural damage to the aircraft.

The output 159 can also or alternatively be used to brief maintenance crew or flight crew on the ground that a mode of aircraft operation has taken place that caused identified structural damage to the aircraft. The maintenance crew can then use information from the output 159 to check the identified location of the damage. The output 159 can be the output used by the pilot, or the maintenance crew can couple a device to the output to receive the output information.

Figure 10:
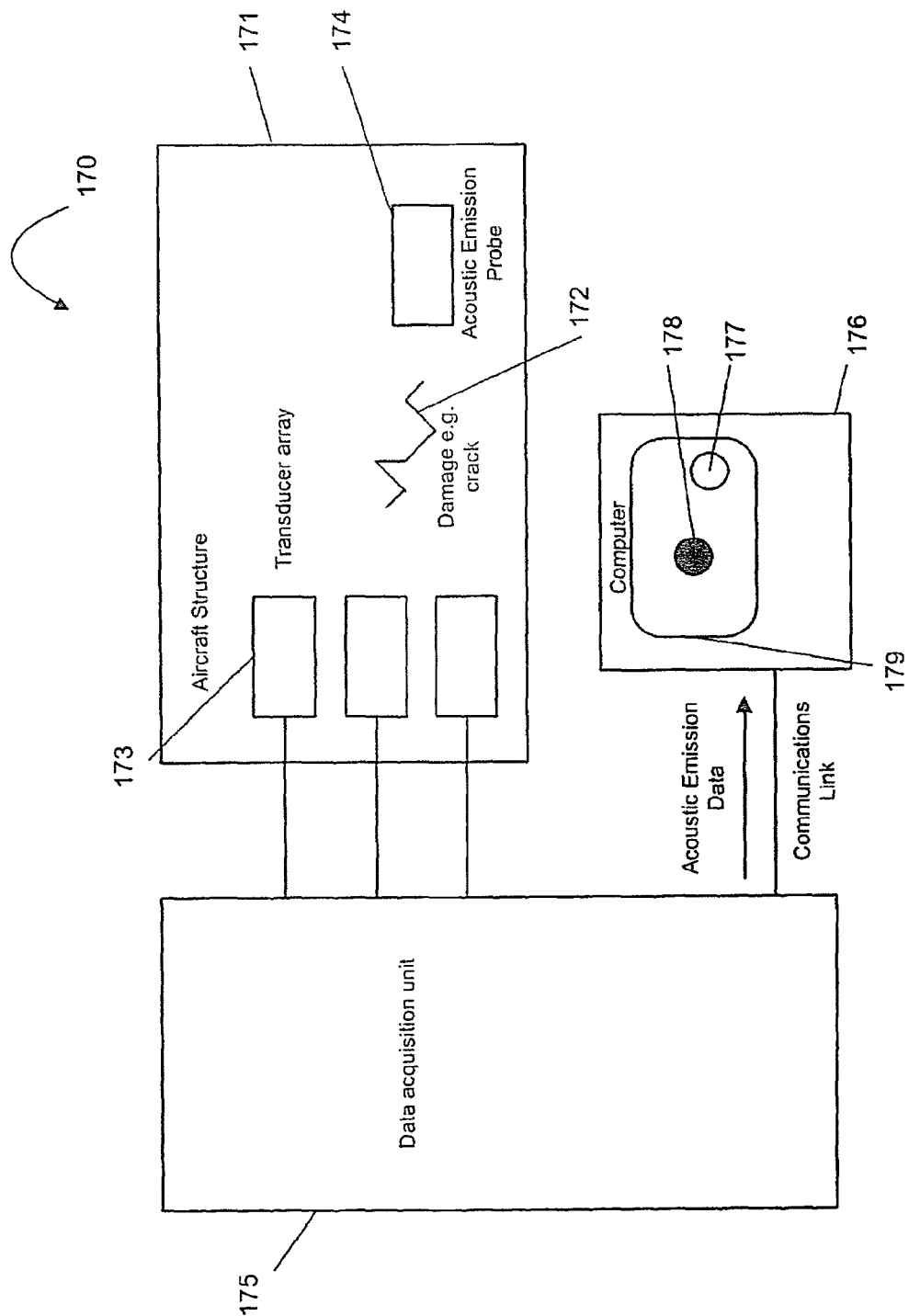
FIG. 10 is a schematic diagram of an acoustic integrity monitoring system for use in confirming a site of structural damage according to a fourth embodiment of the present invention.

A method and system of a fourth embodiment of the present invention for confirming a source of structural damage in a structure will now be described with reference to FIGS. 10 and 11. FIG. 10 shows a system 170 for confirming a source of structural damage. The system comprises sensors 173 acoustically coupled to a structure 171. The sensors are connected to a data acquisition unit 175, as shown in FIG. 2 and described above. The data acquisition unit 175 is connected to a computer 176. An acoustic emission source 174 is provided to generate acoustic emissions in the aircraft structure 171.

Figure 11:
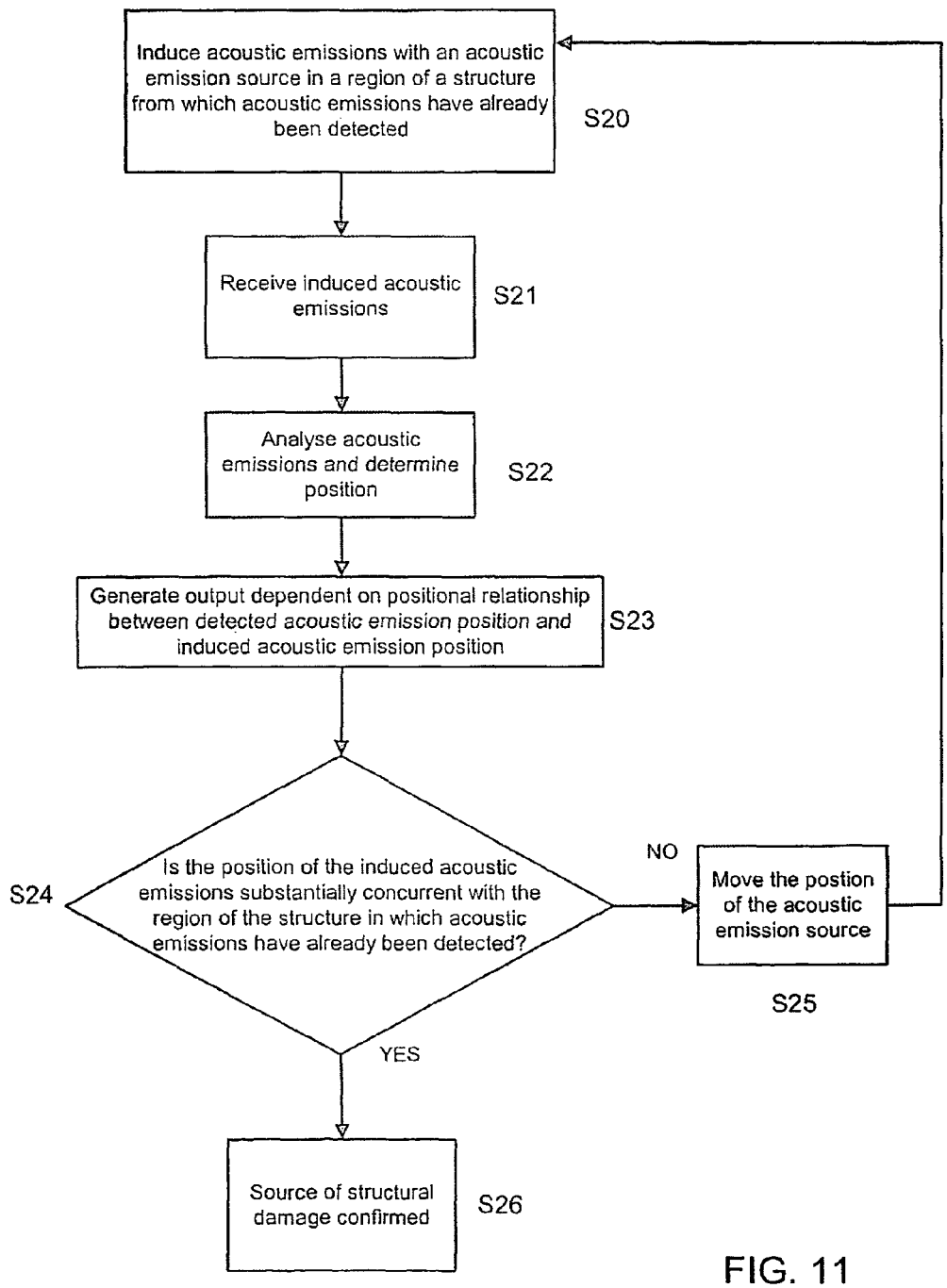
FIG. 11 is a flow diagram of a method used to confirm a site of structural damage.

FIG. 11 shows a flow diagram representing a method for confirming a source of structural damage in a structure. Acoustic emissions are initially detected from a region of damage 172 by known methods and the position of the acoustic emissions is recorded. In this embodiment the prior art method such as that described with reference to FIG. 2, or the method of the second embodiment can be used. The damage information is recorded for example during use. At a maintenance time, the acoustic emission source 174 is then used to induce acoustic emissions in the region of structural damage 172 (step S20). The induced acoustic emissions are detected by the sensors 173 (step S21) and filtered and processed by the data acquisition unit 175 by known methods to obtain acoustic emission data. The acoustic emission data is then analysed by the computer 176 in real time and the position on the structure of the induced acoustic emissions is determined (step S22). An output is then generated dependent on the positional relationship between the detected acoustic emission position and the induced acoustic emission position (step S23). It is possible to plot the position of the induced acoustic emissions. The computer can then produce a plot on the screen 179 showing the relative positions of the induced acoustic emissions and the original detected acoustic emission signal. Alternatively or in addition an audible output can be generated indicating that the induced acoustic emissions are in the proximity of the original detected signal. The position of the induced acoustic emissions is represented by the dot 177 and the position of the original detected acoustic emission signal is represented by the dot 178. If it is determined that the position of the induced acoustic emissions is substantially concurrent with the region of the structure in which acoustic emissions have already been detected (step S24) then this is the position on the structure where the structural damage is located and the source of the structural damage is confirmed (step S26). If the screen 179 is used then the location of the structural damage will be confirmed when the dot 177 overlaps with the dot 178.

However, if it is determined at S24 that the position of the induced acoustic emissions and the region of the structure in which acoustic emissions have already been detected are not substantially concurrent then the acoustic emission source is moved to a different position on the structure (step S25). Steps S20 to S24 are then repeated until the position on the structure where the structural damage is located is confirmed. In this way a closed-loop method for locating the source of structural damage and considerably reduce errors in the location of the damage is provided. Therefore it is not necessary to use the model of acoustic paths to spatially correct the acoustic emissions originally detected from the region of the damage. However the model may be used to narrow down the region in which acoustic emissions are required to be induced by the acoustic emission source.

The computer 176 which is used to control the acoustic emission source 174 and analyse the resulting data can be connected to the data acquisition unit 175 via a communications link. The communications link could either be wired or wireless. A wireless link would enable the computer 176 and the acoustic emission source 174 to be used in less accessible locations.

The acoustic emission source can be a source that is adapted to move over the structure in the x y, and z directions in order to home in on the structural damage. The computer 176 can generate an audible tone that increases in pitch as the source homes in on the damage so that the user of the system can locate the damage without looking at a display.

Unlike a Hsu-Neilson source, which can only be used once, the source used as the acoustic emission source in this embodiment is capable of repeatedly inducing acoustic emissions in a structure.

In addition, the acoustic emission source is also capable of generating a range of signals with different rise times, amplitudes, durations and frequencies in order to simulate different types of damage in a range of materials. Therefore, once the position of the structural damage has been confirmed, the source can then be used to characterise the damage by simulating acoustic emissions in the region of the damage. For example, acoustic emissions associated with cracking could be simulated at the tips of a crack on a structure. The data obtained from a position of structural damage in this way can then be used to correlate acoustic emission activity originating from the position of structural damage on a vehicle structure with causal modes of operation to provide real time correlation data that can be used during operation.

In this embodiment of the present invention, the acoustic emission source is used to confirm the location already determined by the system. If a model of the acoustic paths is not used, the position indicated by the system may be incorrect due the lack of homogeneity of the structure. However, the same process is performed on the induced acoustic emission and thus the same error occurs. Thus even though the system indicates to an operator to place the source in a position, when the source induces acoustic emissions at the indicated position, because of the position determination error, the detected position will not be correct and the signature will not match the signature from the damage. Thus in this embodiment the use of the emission source enables the correct position to be determined by moving the source until the positions detected are concurrent.

If the embodiment uses the model to correct for inhomogeneities in the structure, the above described positional errors will not occur. However, the model only includes data for discrete positions and hence using the model only an approximate location for the damage can be given corresponding to a position. For example, if the model is built by using acoustic emission positions in the array which are spaced 10 cm apart, the determined location of the damage will be given as one of these positions and has an error of ±5 cm.

Thus in one embodiment the acoustic emission source can be used not simply to confirm the location but instead to more accurately locate the damage. In this embodiment, the source is positioned at the determined approximate location of the damage. The detected emissions from the source are then processed and compared with the processed detections for the damage. The source can then be moved until the processed detections e.g. $\Delta t$ values match. This gives an accurate location of the damage which is an interpolated position to the positions in the model.

In this embodiment the detected emissions from the source can be used to enhance the model. If the position of the source is known, the processed detections for the known positions can be used to populate the model at additional positions intermediate the original model positions. This increases the ability of the model to provide more accurate damage locations in the regions of previously detected damage. Thus after the maintenance personnel have performed the damage location, the next time the structure is used, the ability to accurately locate damage using the model in the region of previous structural damage is improved.

The model can also be used to assist the maintenance crew in the location of the damage location using the approximate location provided from use of the model. In the model there are processed parameters for each position. Thus an approximate damage location will have processed parameters e.g. $\Delta t$ values for surrounding positions. The $\Delta t$ values for the approximate location (corresponding to one position) and for surrounding positions can be used to determine $\Delta t$ gradients by extrapolation between the positions. By comparison of the gradients with the $\Delta t$ values for the emissions from the source, the direction of movement of the source can be determined to assist in the rapid location of the accurate location of the site of damage.

Figure 12:
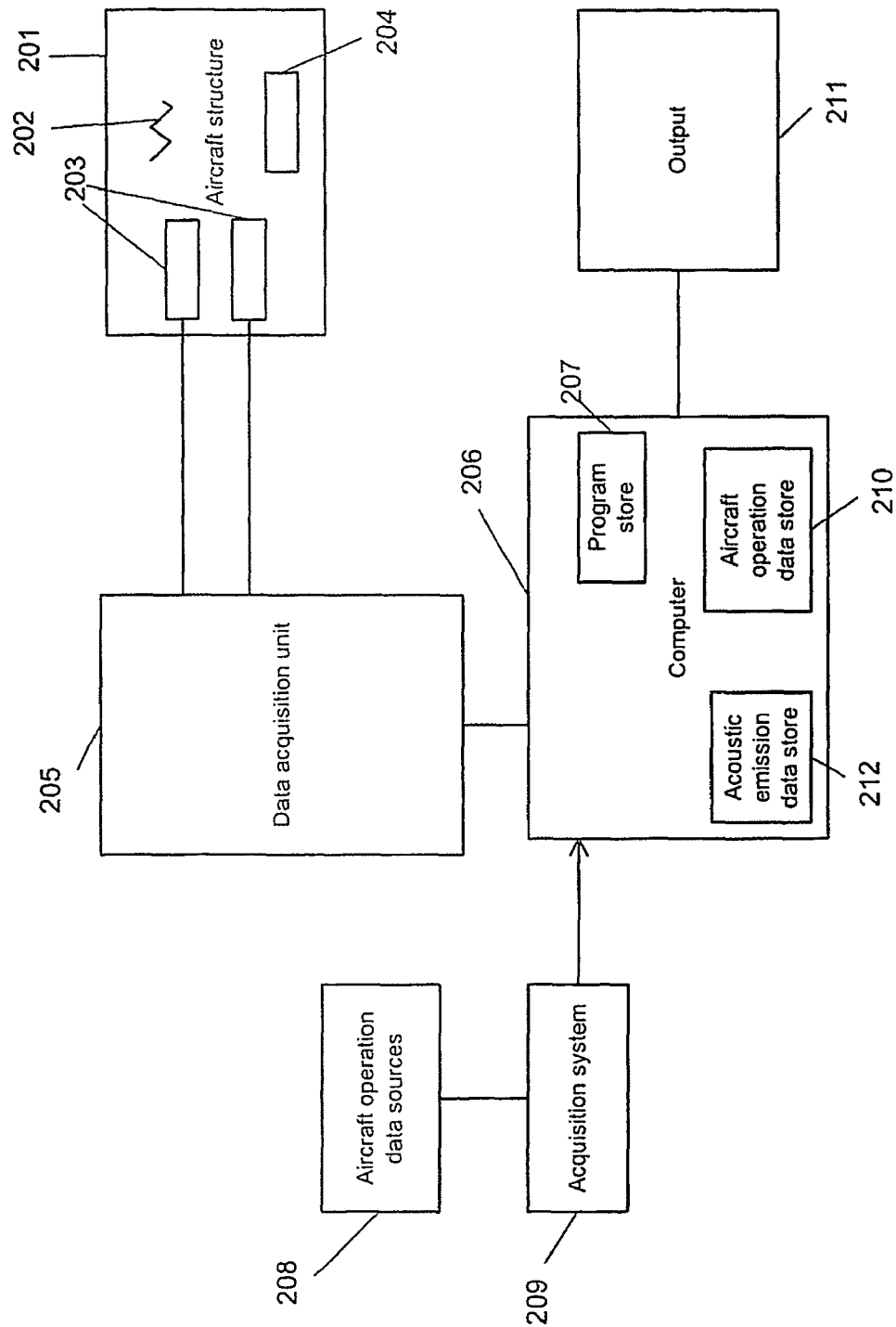
FIG. 12 is a schematic diagram of an acoustic integrity monitoring system according to a fourth embodiment of the present invention.

A fifth embodiment of the present invention will now be described with reference to FIGS. 12 and 13. FIG. 12 is a schematic diagram of a system for checking a region of structural damage in an aircraft to correlate the structural damage with operational modes causing the structural damage. An array of sensors 203 are acoustically coupled to an aircraft surface 201. The sensors are connected to a data acquisition unit 205. The data acquisition unit 205 is connected to a computer 206, which comprises an acoustic emission data store 212, a program store 207 and an aircraft operation data store 210. The aircraft operation data store 210 receives data from the acquisition system 209, which is connected to the aircraft operation data sources 208. An acoustic emission source 204 is provided which is capable of generating acoustic emissions. An output device 211 is provided to output correlation information to air crew or ground staff.

Figure 13:
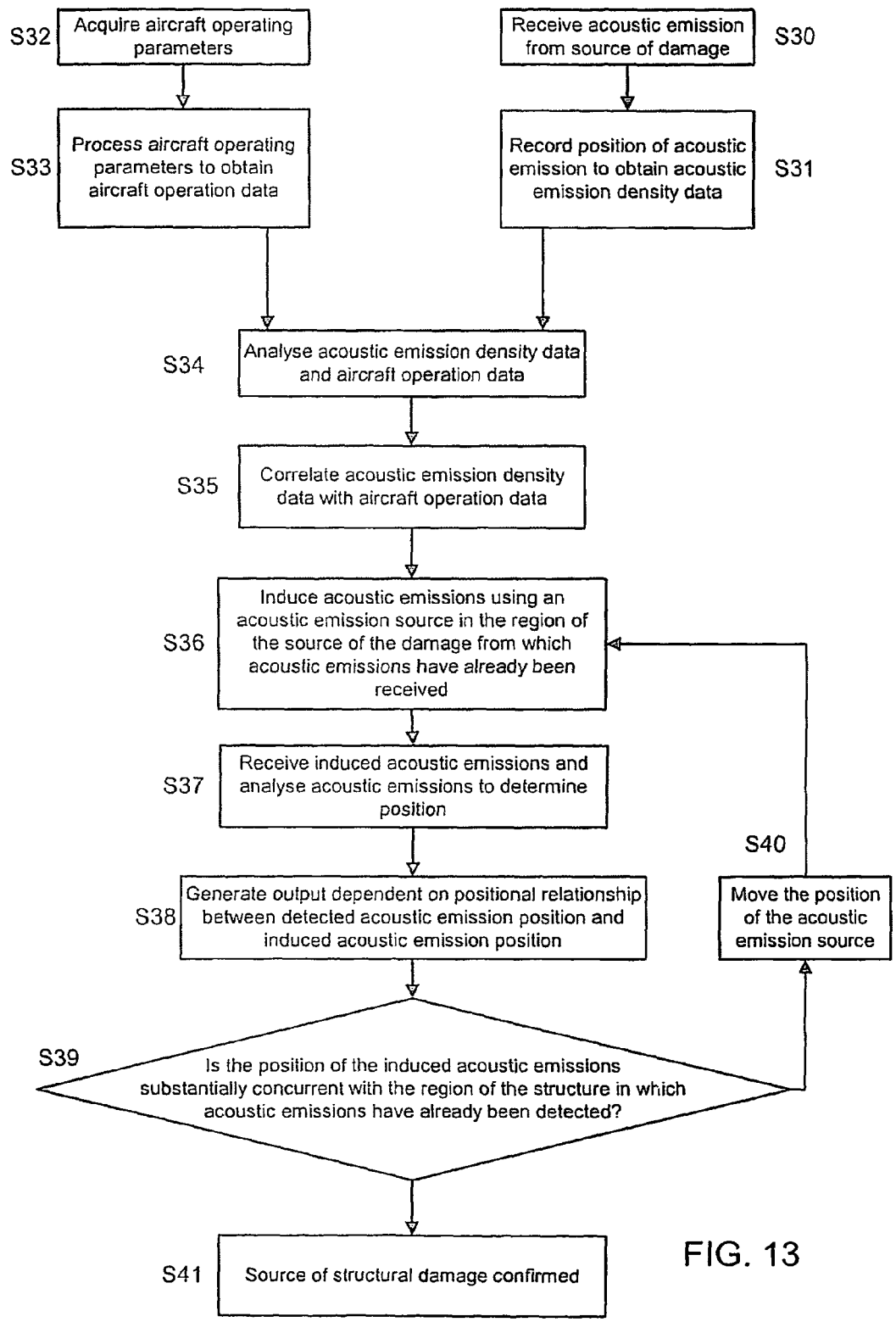
FIG. 13 is a flow diagram of a method of checking a region of structural damage in an aircraft structure to correlate the structural damage with events causing the structural damage.

A flow diagram of the process carried out by the system in FIG. 12 is shown in FIG. 13. Acoustic emissions are received by the sensors 203 from a region of structural damage 202 (step S30). The acoustic emissions undergo filtering and processing in the data acquisition unit 205, using the apparatus shown in FIG. 2, and acoustic emission data is obtained and stored in the acoustic emission data store 212. The position of acoustic emissions on the structure is given by the acoustic emission data and recorded in the acoustic emission data store 212 (step S31).

Aircraft operation data is obtained from the aircraft operation data sources 208 and acquired by the acquisition system 209 (step S32). Aircraft operation data sources are sources of data about aircraft operation parameters and can be, for example, altimeters or strain gauges. The aircraft operation data is processed by analysis software in the program store (207) located in the computer 206 and stored in the aircraft operation data store 210 (step S33). The aircraft operation data is obtained, acquired and processed in time synchronisation with the acquisition of acoustic emission data, while the aircraft is in operation. The acoustic emission data from the acoustic emission data store 212 and aircraft operation data from the aircraft operation data store 210 is then analysed using analysis software in the program store 207 (step S34) to correlate structural damage 202 with one or more modes of aircraft operation (step S35).

The acoustic emission source 204 is then used to induce acoustic emissions in the region of the structural damage 202 as determined from the received acoustic emissions from the region (step S36). The induced acoustic emissions are detected by the sensors 203), filtered and processed by the data acquisition unit 205 using known filtering and processing apparatus illustrated in FIG. 2. The acoustic emission data is analysed by the computer 206 using analysis software stored in the program store 207 in real time and the position on the structure of the induced acoustic emissions is determined (S37). An output device 211 then generates an output dependant upon the positional relationship between the detected acoustic emissions for the structural damage and the induced acoustic emissions (step S38). If the position of the induced acoustic emissions is substantially concurrent with the region of the structure in which acoustic emissions have already been detected (step S39) then this is the position on the structure where the structural damage is located and in step S41 an output is generated on the output device 211 to indicate this. The maintenance crew are thus able to confirm the damage position by inspection e.g. a visual inspection to validate the process. If the positions are not substantially concurrent (step S39), the source 204 is moved to a new position (step S7) and the process returns to step S36 to repeat the location confirmation.

A method for defining an area of the structure and correlating the structural damage with causal modes of vehicle operation is therefore provided. The source is used to define the x, y and z extents of the area of interest e.g. by inducing acoustic emission signals at either ends of the lower spar cap. This area could be defined before or after the in-flight acoustic emission data has been captured. The area may be defined even before the damage has occurred. It is not necessary to use the model of acoustic paths to spatially filter the acoustic emissions originally detected from the region of the damage but errors in the determined position of structural damage can be reduced further if the model is used. This method can be used with any structure but is particularly useful for locating structural damage in aircraft, where damage can be catastrophic.

In addition the damage can be characterised by using the source to simulate different types of damage with varying degrees of severity, for example fretting, cracking and rubbing in the located source of the damage. This means that as well as indicating that one or more modes of aircraft operation caused structural damage to an aircraft, for example the output 211 can also provide information indicating which particular mode or modes of aircraft operation cause a certain type of structural damage. This is particularly useful, as it can provide a means for assessing the severity of structural damage that performing a certain aircraft manoeuvre is likely to cause.

The output 211 can be used as to warn pilots during (or after) flight that they have performed a manoeuvre with the aircraft that has caused structural damage to the aircraft and advise that the structure of the aircraft has been compromised as a result. Warning pilots could take place by adapting the output 211 to be a display panel for displaying information indicating the modes of aircraft operation taking place when a certain type of structural damage occurred, the location of the structural damage and the result of the damage on the aircraft's structure and/or performance. The pilot can then decide whether to modify his behaviour and change the mode of aircraft operation to contain the damage based on the warning. Alternatively, there can also be a system provided for receiving the output 211 and preventing the pilot from performing the particular manoeuvre that caused identified structural damage to the aircraft.

The output 211 can also be used to brief maintenance crew or flight crew on the ground that a mode of aircraft operation has taken place that caused identified structural damage of a particular type and/or severity to the aircraft. The maintenance crew can then use the information from the output 211 to check the identified location of the damage. The flight crew can use the information to modify their flying behaviour during the next flight.

This embodiment can also be used with the model of acoustic paths to further increase the accuracy in the detected location of the site of structural damage.

Thus one aspect of the invention provides the advantage of locating a site of structural damage in a structure that takes into account the effects of structural inhomogeneities that lead to errors in calculation of $\Delta t$ values, the variation of the speed of propagation of acoustic waves in inhomogeneous structures and the different modes of acoustic propagation.

Another aspect of the present invention provides the advantage that the cost of the system may be reduced by using an optimised sparse array of sensors to detect acoustic emissions from the structural damage 137.

Yet another advantage of an aspect of the present invention is that it can provide information to vehicle operators that structural damage has occurred to a vehicle, as well as an indication of the location of the damage and that a particular mode of vehicle operation caused the structural damage.

Although the present invention has been described hereinabove with reference to specific embodiments, the present invention is not limited to the specific embodiments and modifications will be apparent to a skilled person in the art which lie within the spirit and scope of the present invention. For example, in the third embodiment, the system and method for correlating structural damage with causal modes of structure use is not limited to employing a model of acoustic paths for spatially filtering acoustic emissions detected from a structure. Any of the embodiments described hereinabove can be used in any combination.

Although embodiments of the present invention have been described with reference to an aircraft structure, the present invention is applicable to any engineering structure, including static structures such as bridges and oil rigs. In such static structures a mode of operation comprises a mode of use e.g. loading on a bridge or drilling operations performed on an oil rig.

Although in the embodiments the acquisition system and the computer for analysing the data are shown as separate units, the can of course be combined or their function provided by any combination of units. The acquisition system can be implemented either in software or hardware.

Any aspect of the present invention can be used in conjunction with any other aspect and thus the present invention encompasses a method and system using any combination of the aspects briefly outlined above. Modifications that lie within the spirit and scope of the present invention will be apparent to a skilled person in the art.

Therefore, having thus described the invention, at least the following is claimed:

1. A method of determining a physical location of structural damage in a structure, the method comprising:
   detecting acoustic emissions from said physical location of structural damage using a plurality of acoustic sensors arranged on said structure; and using a processor to process the detected acoustic emissions using a model characterizing effects of acoustic paths between a plurality of positions on said structure and said acoustic sensors to determine said physical location of said structural damage;

wherein the model includes data identifying different types of acoustic emissions and corresponding types of structural damage, and said processing includes determining said physical location and identifying structural damage using the model data.

2. The method of claim 1, wherein the processing comprises comparing processed parameters determined from the detected acoustic emissions with the model.

3. The method of claim 1, wherein said acoustic emissions are processed to determine at least one of differences in times of arrival of said acoustic emissions at said sensors, wave-shape information, emission duration, amplitudes of said acoustic emissions and rise times of said acoustic emissions; and said model comprises at least one of differences of times of arrival of said acoustic emissions at said sensors, wave-shape information, emission duration, amplitudes of said acoustic emissions and rise times of said acoustic emissions for each position.

4. The method of claim 1, further comprising storing acoustic emission data obtained by said processing of the detected acoustic emissions.

5. The method of claim 1, wherein said model includes wave-shape information for different types of structural damage, and said processing includes determining wave-shape information for the detected acoustic emissions and comparing the determined wave-shape information with the model to identify the structural damage.

6. The method of claim 1, wherein said acoustic emissions comprise bursts of acoustic emissions.

7. The method of claim 1, further comprising determining and storing physical data on the structure when acoustic emissions are detected.

8. The method of claim 6, wherein said processing includes accumulating bursts having similar time of arrival properties, and when a threshold is reached for a group of bursts having similar time of arrival properties, determining a location of origin of the bursts and the structural damage using the model and generating an indication of structural damage.

9. The method of claim 6, wherein said processing includes determining a physical location of origin of each burst using the model, accumulating bursts having similar physical locations of origin, and when a threshold is reached for a group of bursts having similar physical locations of origin, generating an indication of structural damage.

10. A system for determine a physical location of structural damage in a structure, the system comprising:

a plurality of sensors for detecting acoustic emissions from said physical location of structural damage; and a data processing system for processing acoustic emissions detected by said sensors using data defining a model characterizing effects of acoustic paths between a plurality of positions in said structure and said acoustic sensors;

wherein said model data includes data identifying different types of acoustic emissions and corresponding types of structural damage, and said data processing system is adapted to determine said physical location and identify structural damage using the model data.

11. The system of claim 10, wherein the data processing system is adapted to compare processed parameters determined from detected acoustic emissions with the data defining the model.

12. The system of claim 10, wherein said data processing system is adapted to process said acoustic emissions detected by said sensors to determine at least one of differences in times of arrival of said acoustic emissions at said sensors, wave-shape information, emission duration, amplitudes of said acoustic emissions and rise times of said acoustic emissions; and said model comprises at least one of times of arrival of said acoustic emissions at said sensors, wave-shape information, amplitudes of said acoustic emissions and rise times of said acoustic emissions for each position.

13. The system of claim 10, further comprising a store for storing acoustic emission data obtained by said processing of the detected acoustic emissions.

14. The system of claim 10, wherein said acoustic emissions comprise bursts of acoustic emissions, said data processing system is adapted to accumulate bursts having similar time of arrival properties, and when a threshold is reached for a group of bursts having similar time of arrival properties, to determine a location of origin of the bursts and the structural damage using the model data, and to generate an indication of structural damage.

15. The system of claim 10, wherein said acoustic emissions comprise a burst of acoustic emissions, said data processing system is adapted to determine a physical location of origin of each burst using the model data, to accumulate bursts having similar physical locations of origin, and when a threshold is reached for a group of bursts having similar physical locations of origin, to generate an indication of structural damage.

16. The system of claim 10, further comprising an arrangement for determining and storing physical data on the structure when acoustic emissions are detected.

17. The system of claim 13, wherein said model data includes wave-shape information for different types of structural damage, and said data processing system is adapted to determine wave-shape information for the detected acoustic emissions and compare the determined wave-shape information with the model data to identify the structural damage.

* * * * *